(12) United States Patent
Prater et al.

(10) Patent No.: US 6,196,971 B1
(45) Date of Patent: Mar. 6, 2001

(54) CHORD PROPAGATION VELOCITY MEASUREMENT SYSTEM AND METHOD FOR AN ULTRASOUND IMAGING SYSTEM

(75) Inventors: David M Prater, Andover; Joel Friedman, Somerville, both of MA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/285,842

(22) Filed: Apr. 2, 1999

(51) Int. Cl.[7] ........................................... A61B 8/02
(52) U.S. Cl. ................................................ 600/450
(58) Field of Search ................................... 600/438, 437, 600/443, 447, 441, 442, 485, 483, 504–507; 73/629, 1 DV

(56) References Cited

U.S. PATENT DOCUMENTS

| | | | |
|---|---|---|---|
| 5,107,837 | * 4/1992 | Ophir et al. | 600/437 |
| 5,301,675 | * 4/1994 | Tomita | 600/485 |
| 5,474,070 | * 12/1995 | Ophir et al. | 600/437 |
| 5,517,995 | * 5/1996 | Klepper et al. | 600/447 |
| 5,830,131 | * 11/1998 | Caro et al. | 600/300 |
| 6,023,977 | * 2/2000 | Langdon et al. | 73/629 |

* cited by examiner

Primary Examiner—Marvin M. Lateef
Assistant Examiner—Ali M. Imam

(57) ABSTRACT

A chord propagation velocity measurement (CPVM) system is used in connection with, for example, a brightness-mode (B-mode) or doppler ultrasound imaging system. The CPVM system monitors ultrasound data provided to it by the ultrasound imaging system and enhances the functionality of the ultrasound imaging system by providing a chord propagation velocity (CPV) associated with a body region, such as a blood vessel in a living thing. The CPV is indicative of the stiffness of the body region. In architecture, the CPVM system includes a tissue processor connected to the scanner of the ultrasound system designed to analyze each acoustic scan line and to determine a category (type of region, for example, blood or tissue) for each point along each acoustic scan line. A display produces an image generated from acoustic scan lines. A user input mechanism permits a user to identify a region of interest in the image. The tissue processor produces samples based upon the region of interest in the image. A CPV determination system, which is connected to the tissue processor, acquires a plurality of the samples from different subregions along a longitudinal span of the region for each of a plurality of different cycles, derives a plurality of composites, one for each subregion, by combining corresponding samples from different cycles, and produces a CPV based upon the plurality of composites. Preferably, the CPV is displayed, printed, or otherwise output by the CPVM system to the user of the ultrasound imaging system in real time to permit immediate analysis, and evaluation of the body region by the user.

18 Claims, 8 Drawing Sheets

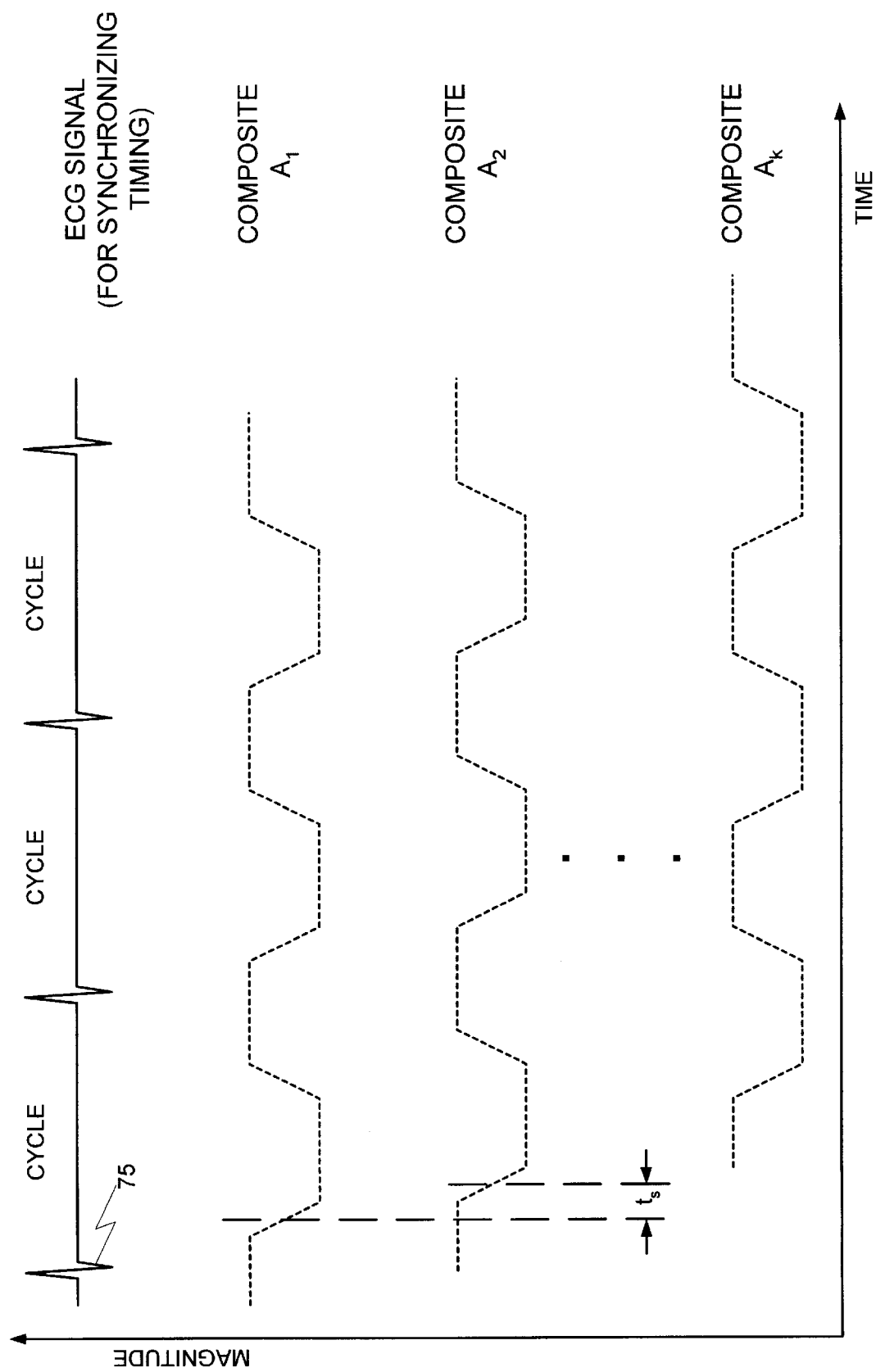

CHORD PROPAGATION VELOCITY MEASUREMENT SYSTEM AND METHOD FOR AN ULTRASOUND IMAGING SYSTEM

FIELD OF THE INVENTION

The present invention generally relates to ultrasound imaging systems, and more particularly, to a chord propagation velocity measurement (CPVM) system and method for producing a chord propagation velocity (CPV) associated with a part in a body, for example but not limited to, a blood vessel in a living thing. In the context of a blood vessel, the CPV is indicative of the vessel stiffness, which is an important determinant of vessel health.

BACKGROUND OF THE INVENTION

The stiffness of a blood vessel in a living thing, particularly, a human being, can be used in assessing the health of the blood vessel. Presently, there are at least two known techniques for estimating vessel stiffness.

One technique involves assessing vessel stiffness by measuring the internal pressure within a vessel and dimensional changes resulting from pressure changes. However, it is very difficult to measure internal pressure within a vessel inside a body, and moreover, systems and apparatus to make external pressure measurements are not easily calibrated and require compressing the vessel.

Another technique for estimating vessel stiffness entails measuring a pressure propagation velocity. The pressure propagation velocity is a measure that is known to be very closely correlated with vessel stiffness and is a measure of the velocity with which a pressure pulse propagates along a vessel.

Both of the foregoing techniques require one or more pressure measurements of some sort that is very difficult to implement in vivo. To make these measurements, pressure transducers are placed externally on the body, e.g., on the skin of a person's body, and are monitored by an appropriate monitoring system in order to estimate pressure changes in vessels under the skin. There are many corrupting influences and limitations of this procedure. Because the pressure transducers are usually placed a large distance apart, for example, a half of a meter in some cases, local regions of vessels cannot be effectively isolated and analyzed for, for example, plaque formation, thrombi (blood clots), aneurysms, etc. Furthermore, when pressure transducers are used externally on a body, only vessels near the surface of the body can be analyzed. In other words, internal vessels, such as the important abdominal aorta associated with the heart, which degrades in most elderly people, cannot be analyzed.

Thus, a heretofore unaddressed need exists in the industry for a way to better quantitatively measure vessel stiffness, to thereby assess vessel health in a living thing.

SUMMARY OF THE INVENTION

The present invention provides a chord propagation velocity measurement (CPVM) system and method used in connection with, for example, a brightness-mode (B-mode) or doppler ultrasound imaging system. The CPVM system monitors ultrasound data provided to it by the ultrasound imaging system and enhances the functionality of the ultrasound imaging system by providing a chord propagation velocity (CPV) associated with a body part, such as a blood vessel in a living thing. The CPV is indicative of the stiffness of the body part.

In architecture, the CPVM system includes a tissue processor connected to the scanner of the ultrasound system designed to analyze each acoustic scan line and to determine a category (type of region, for example, blood or tissue) for each point along each acoustic scan line. A display produces an image generated from acoustic scan lines. A user input mechanism permits a user to identify a region of interest in the image. The tissue processor produces samples from different subregions of the region of interest in the image. In the context of a B-mode ultrasound imaging system, the samples are cross sectional areas $A_i$ and/or chords $h_i$. In the context of a doppler ultrasound imaging system, the samples are changes in the cross sectional areas $\Delta A_i$ and/or chords $\Delta h_i$.

A CPV determination system, which is connected to the tissue processor, acquires a plurality of the samples along a longitudinal span of the region for each of a plurality of different cycles, derives a plurality of composites, one for each subregion, by combining corresponding samples from different cycles, and produces a CPV based upon the plurality of composites. The CPV can be displayed, printed, or otherwise output by the CPVM system to the user of the ultrasound imaging system, optionally, continuously updated in real time, to permit immediate analysis, and evaluation of the body part by the user.

The present invention can also be conceptualized as providing a method for quantifying stiffness of a part of a body. In this regard, the method can be broadly stated by the following steps: acquiring a plurality of measured samples from different subregions along a longitudinal span of the body part for each of a plurality of different cycles; deriving a plurality of composites, one for each subregion, by combining corresponding samples from different cycles; and producing a CPV based upon the plurality of composites, the CPV being indicative of the stiffness.

Other features of the invention will become apparent to one with skill in the art upon examination of the following drawings and detailed description. These additional features and advantages are intended to be included herein within this description and protected by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views. Finally, graphs are shown schematically for simplicity.

FIG. 5 is a graph (magnitude versus time) showing data (e.g., areas along the slice) measured over a plurality of cycles (e.g., ECG cycles), from which composites are derived and utilized to compute the CPV along the blood vessel of FIG. 4;

DETAILED DESCRIPTION OF THE PREFERRED EMBODIMENT

Figure 1A:
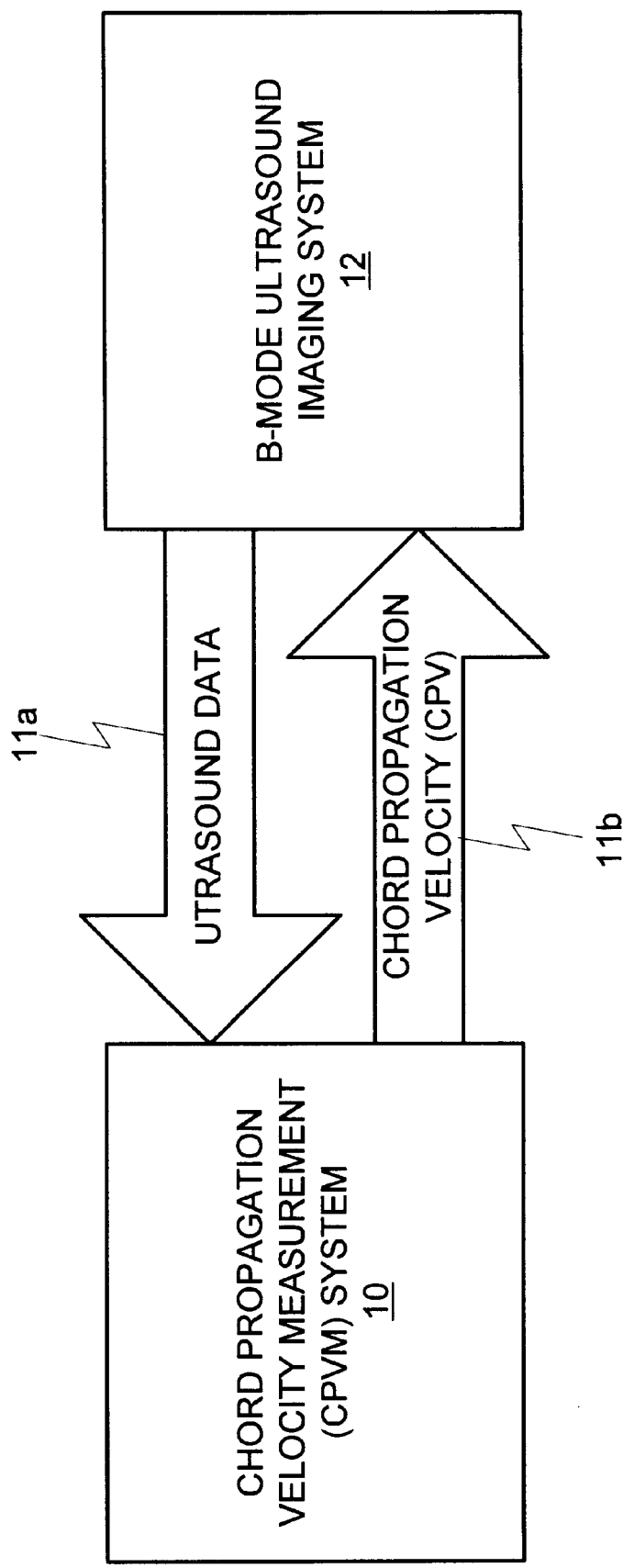
FIG. 1A is a high level block diagram of the chord propagation velocity (CPV) measurement (CPVM) system of the present invention, which is associated and in electrical communication with a brightness-mode (B-mode) ultrasound imaging system.

By way of a high level block diagram, FIG. 1A shows the chord propagation velocity measurement (CPVM) system 10 of the present invention used in connection with, for example but not limited to, a brightness-mode (B-mode) ultrasound imaging system 12. Generally, the CPVM system 10 monitors ultrasound data 11a provided to it by the B-mode ultrasound imaging system 12 and enhances the functionality of the B-mode ultrasound imaging system 12 by providing a chord propagation velocity (CPV) 11b associated with a body part, such as a blood vessel in a living thing. As mentioned, the CPV is indicative of the stiffness of the body part. The CPV can be displayed, printed, or otherwise output by the CPVM system 10 to the user of the B-mode ultrasound imaging system 12, optionally in real time, to permit immediate analysis, and evaluation of the body part by the user.

In architecture, the B-mode ultrasound imaging system 12 can be any suitable, conventional or custom system and can be implemented in hardware, software, firmware, or a combination thereof. Many different types are known in the art and are commercially available. Furthermore, the CPVM system 10 of the present invention can be implemented in hardware, software, firmware, or a combination thereof.

Figure 1B:
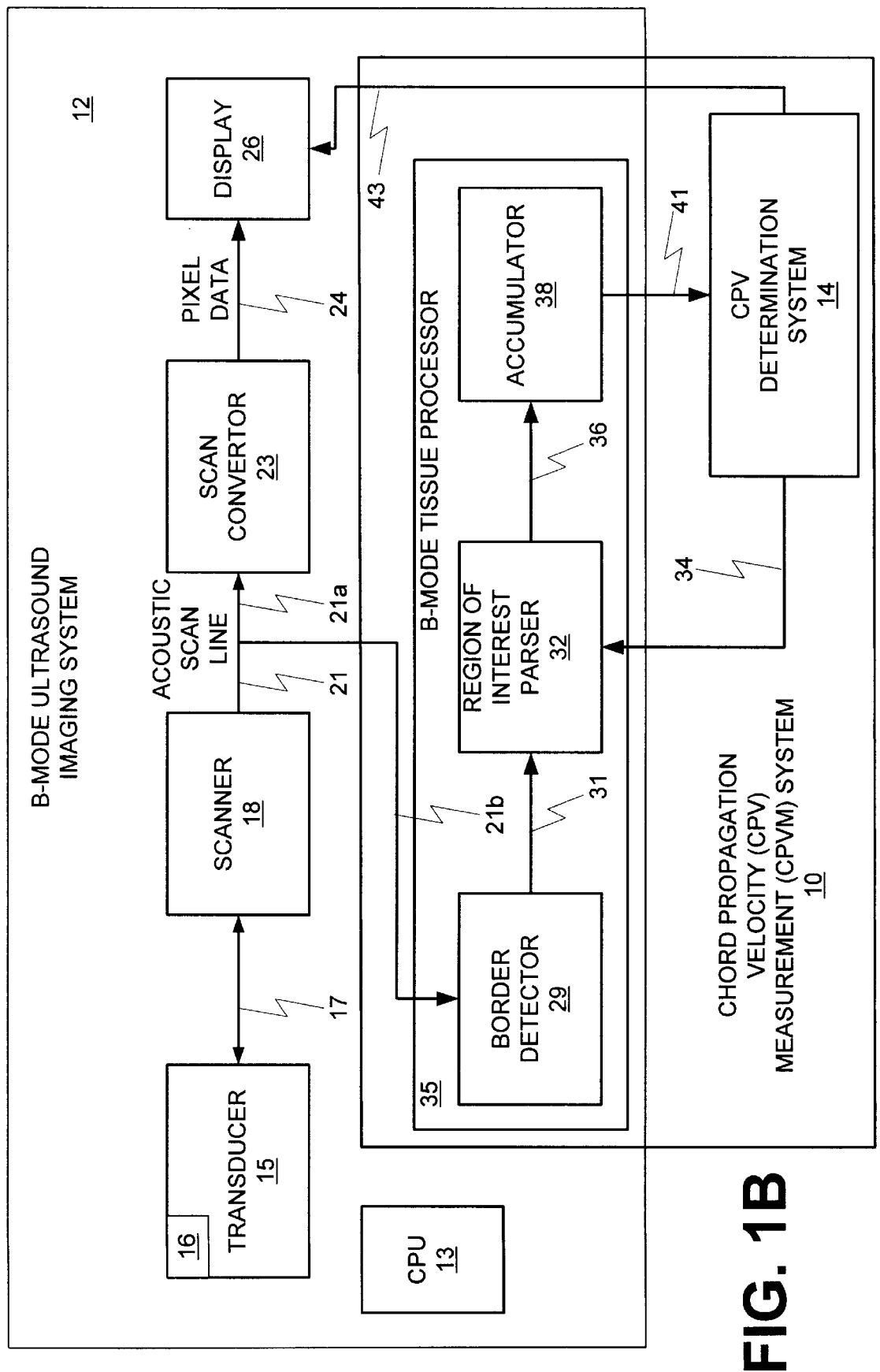
FIG. 1B is a low level block diagram of examples of possible implementations of the CPVM system and of the B-mode ultrasound imaging system of FIG. 1, as interconnected.

FIG. 1B is a low level block diagram of examples of possible implementations of the CPVM system 10 and of the B-mode ultrasound imaging system 12 of FIG. 1A, as interconnected, or in electrical communication. With reference to FIG. 1B, in this example implementation, the B-mode ultrasound imaging system 12 is a SONOS 5500 system manufactured by and commercially available from the Hewlett-Packard Company, U.S.A. The system 12 is a computer-based system having a plurality of hardware elements, for example, programmable logic arrays and/or ASICs, for processing data in generally a pipeline successive processing manner and a conventional central processing unit (CPU) 13 designed to control the operation and timing of the various elements and data flow of the ultrasound imaging system 10, pursuant to suitable control software (not shown for simplicity).

The ultrasound imaging system 12 includes an ultrasonic transducer 15, or probe, configured to emit and receive ultrasound signals, or acoustic energy, respectively to and from an object under test (e.g., a body or a patient when the ultrasound imaging system 10 is used in the context of a medical application). Many types of transducers 15 are known in the art and are suited for use in connection with the present invention. For example, a suitable transducers 15 are a linear-type transducer, sector transducer, and a curved linear array (CLA) transducer.

In the preferred embodiment, the transducer 15 is a linear-type transducer. The linear transducer has a movable aperture 16 that is moved back and forth along a linear path in order to acquire acoustic scan lines along the path. Linear transducers are well known in the art. The movable aperture 16 associated with the transducer 15 is essentially a window from which an image is acquired that is created and defined by an array of elements, typically made of a piezoelectric material, for example but not limited to, crystal. Each element is voltage biased and supplied with an electrical pulse or other suitable electrical waveform, causing the elements to collectively propagate an ultrasound pressure wave into the object under test at the aperture location. Moreover, in response thereto, one or more echoes are emitted by the object under test and are received at the aperture 16 of the transducer 15, which transforms the echoes into an electrical signal for further signal processing.

The array of elements associated with the transducer 15 enables the aperture 16, emanating from the transducer array to be linearly steered (during transmit and receive modes) by shift in the phase (introducing a time delay) of the electrical pulses/biasing signals supplied to the separate elements. During transmit, an analog waveform is communicated to each transducer element, thereby causing a pulse to be selectively propagated in a particular direction, at the position of the aperture 16, through the object.

During the receive mode, an analog waveform is received at each transducer element at each aperture position. Each analog waveform essentially represents a succession of echoes received by the transducer element over a period of time as echoes are received along the single beams through the object. The entire set of analog waveforms represents an acoustic scan line, and the entire set of acoustic scan lines represents a single view, or image, of an object and is referred to as a frame.

The transducer 15 is connected to or otherwise is in electrical communication with a suitable ultrasound scanner 18, which is known in the art. The scanner 18 produces acoustic scan lines 21, which are ultimately scan converted for producing picture element (pixel) data. In architecture, as an example, the scanner 18 typically includes a transmit pulser for generating electrical pulses for the transducer 15, one or more preamplifiers for receiving analog electrical echo waveforms from the transducer 15 that are generated by echoes emitted from the object under test, one or more time-gain compensators (TGCs) designed to progressively increase the gain during each acoustic scan line to thereby reduce the dynamic range requirements on subsequent processing stages, one or more analog-to-digital converters (ADCs) configured to convert the analog echo waveforms into digital echo waveforms comprising a number of discrete location points with respective quantized instantaneous signal levels, a beam former connected to the ADCs and designed to receive the multiple digital echo waveforms from the ADCs and combine them to form each signal acoustic scan line, and radio frequency (RF) filters configured to reduce noise in the acoustic scan lines. The scanner 18 outputs acoustic scan lines 21 to a scan converter 23.

The scan converter 23 is in electrical communication with the scanner 18, as illustrated in FIG. 1B. The scan converter 23 is designed to convert the scan lines 21 from one coordinate system to another and to generate an image of the data from a particular vantage point, in order to produce pixel data for display. Generally, the scan converter 23 processes the acoustic scan lines 21 once an entire data frame (set of all acoustic scan lines in a single view, or image/picture to be displayed) has been accumulated by the scanner 18. The process implemented by the scan converter 23 is well known in the art. The scan converter 23 outputs pixels 24 for storage and/or display. In this case, the scan converter 23 is shown driving pixel data 24 to a display 26, as an example.

The display 26, which is in electrical communication with the scan converter 23, is any suitable conventional display device, such as a computer monitor, configured to periodically retrieve the pixel data 24 from the scan converter 23 and drive a suitable screen for viewing of ultrasound images by a user.

The CPVM system 10 in accordance with the preferred embodiment of the present invention comprises B-mode tissue processor 35, which includes a border detector 29, a region-of-interest parser 32, and an accumulator 38, interconnected with a CPV determination system 14. In this example of an implementation, the B-mode tissue processor, including the border detector 29, the region-of-interest parser 32, and the accumulator 38, are implemented in hardware logic, for example, PGAs and/or ASICs within the SONOS 5500 system produced by and commercially available from the Hewlett-Packard Company, while the CPV determination system 14 is implemented via a computer executing suitable software, as will be further described hereinafter, which is connected to the SONOS 5500 system. Furthermore, the tissue processor 35 associated with the SONOS 5500 system as well as with the present invention is described in commonly assigned U.S. Pat. No. 5,195,521, which is incorporated herein by reference. It should be understood that the CPVM system 10 could be implemented in hardware, software, or a combination thereof, as a separate unit from the ultrasound system 12 and used in connection with a wide variety of conventional ultrasound systems.

The border detector 29 is designed to receive and analyze acoustic scan lines 21, 21b from the scanner 18. The border detector 29 analyzes each point along each acoustic scan line 21b in order to determine whether each acoustic scan line 21b has passed from one region to another region in the body under test, for example but not limited to, from a blood region to a tissue region, or vice versa. The border detector 29 categorizes the points into categories corresponding with the regions. Any suitable algorithm can be employed by the border detector 29 in order to determine when a region border has been crossed by an acoustic scan line and what points along the acoustic scan line correspond with what regions. Typically, the algorithm will analyze the brightness level of a point and its neighbors in order to determine which regional category to place the point.

A region-of-interest parser 32 is in electrical communication with the border detector 29. The region-of-interest parser 32 receives the categorized data 31 from the border detector 29, and one or more region-of-interest inputs 34 from the CPVM system 10. The inputs 34 can be predefined or are provided, for example, by a user, and identify the area in an image that is of interest to the user of the system 12. A reason for the region-of-interest parser 32 is that the image may span over several different regions of interest, or parts, e.g., vessels, in which case, the region to be analyzed by the CPVM system 10 needs to be specifically identified and isolated for analysis. In the preferred embodiment, the inputs 34 are communicated to the CPVM system 10 via a mouse, trackball, and/or keyboard, which in turn communicates inputs 34 to the region-of-interest parser 32. In order to identify the region of interest, the user positions a couple of points on the display 26 that define a rectangular box having the region of interest contained therein. Each point can be defined by the user by moving the mouse cursor to a position and either clicking a mouse button or depressing a keyboard key. Many other input schemes are possible, as will be known to one with skill in the art.

An accumulator 38 is in electrical communication with the region-of-interest parser 32 and is designed to receive the parsed categorized data 36 from the parser 32. The preferred embodiment of the accumulator 38 is described in commonly assigned U.S. Pat. No. 5,538,003, the disclosure of which is incorporated herein by reference.

Figure 4:
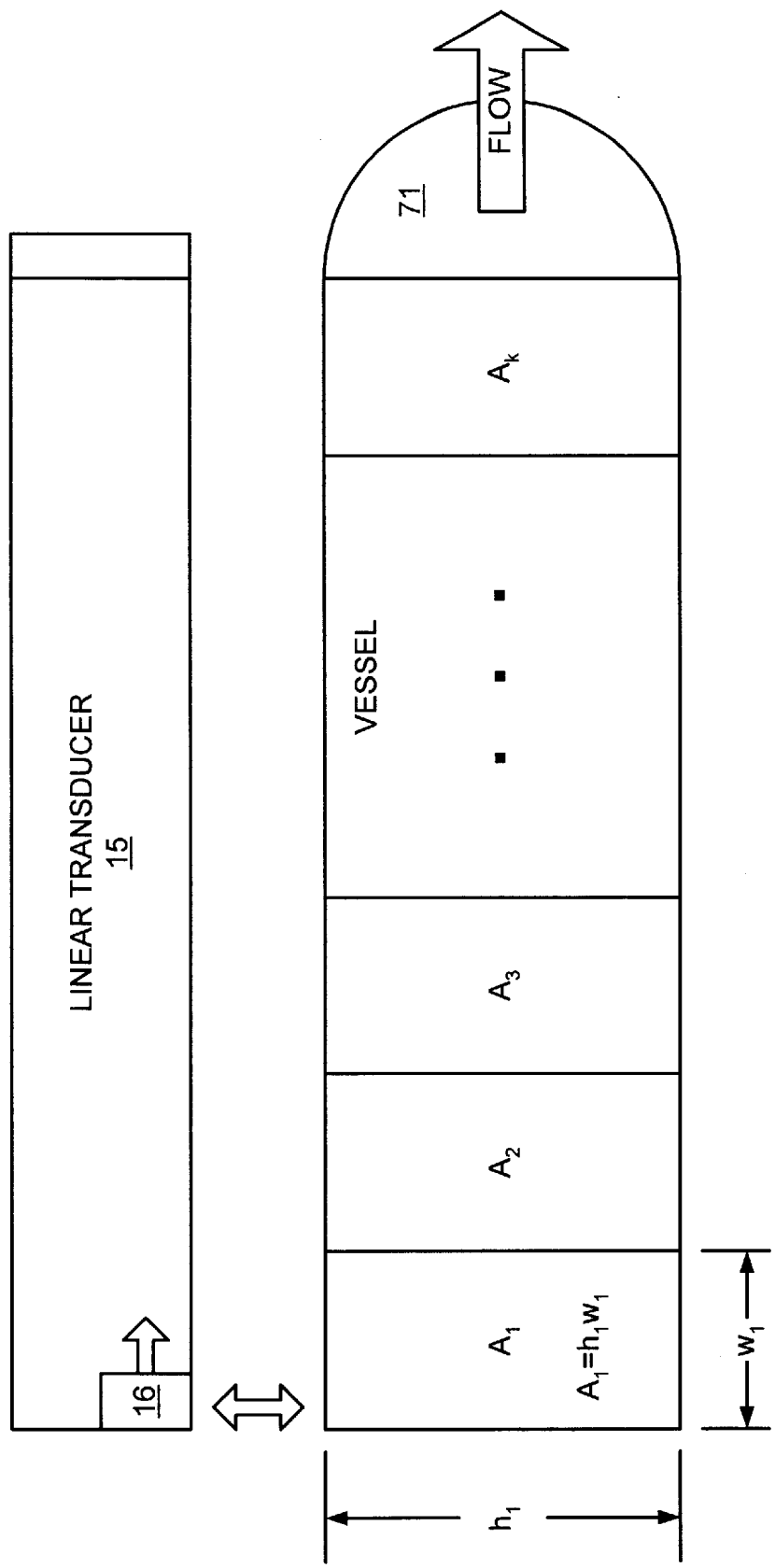
FIG. 4 is a schematic diagram of an image of a longitudinal cross sectional slice taken along the longitudinal axis of a blood vessel, which image is captured by the ultrasound imaging system of FIG. 1 and analyzed by the CPVM system of FIG. 1.

The accumulator 38 is designed to generate a plurality of cross-sectional areas $A_i$ (FIG. 4), where i=1, 2, . . . , k, from the categorized parsed data 36 and forwards the cross-sectional areas $A_i$ to the CPV determination system 14 for further processing to determine the CPV. In the preferred embodiment of the invention, the accumulator 38 produces cross-sectional areas Ai along the longitudinal span of a blood vessel, as is illustrated in FIG. 4. As shown in FIG. 4, the linear-type transducer 15 scans the region of interest, for instance, a length of the longitudinal span of the blood vessel 71, by moving its aperture 16 along a length of the vessel 71. Essentially, the points along each acoustic scan line captures the information relating to the distance $h_i$, referred to as a "chord" herein, and the width $w_i$ is a preset (although it could vary in other implementations) number of acoustic lines. Moreover, each area $A_i$ is calculated by the accumulator 38 by multiplying the corresponding distance $h_i$, by the corresponding width $w_i$.

In an alternative implementation, the accumulator 38 produces the plurality of chords $h_i$, where i=1, 2, . . . , k, from the categorized parsed data 36 and forwards the chords $h_i$ to the CPV determination system 14 for further processing to determine the CPV.

In yet another alternative implementation, the accumulator 38 produces the plurality of areas $A_i$ and chords $h_i$, from the categorized parsed data 36 and forwards both of them to the CPV determination system 14 for further processing to determine the CPV.

Furthermore, in any of the forgoing alternative implementations, each of the areas $A_i$ and chords $h_i$ is time stamped. Any suitable clock may be utilized.

Referring back to FIG. 1B, the CPV determination system 14 is designed to produce a CPV based upon the plurality of cross-sectional areas 41 received from the accumulator 38. Further, the CPVM system 10, particularly, the CPV determination system 14, is designed to communicate the CPV, as indicated by reference arrow 43 to the display 26, as shown in FIG. 1B, so that the user of the system 12 can correlate the CPV with the region-of-interest that was, in the preferred embodiment, identified by the user. As mentioned previously, the CPV 43 is indicative of the stiffness and health of a vessel.

Figure 2:
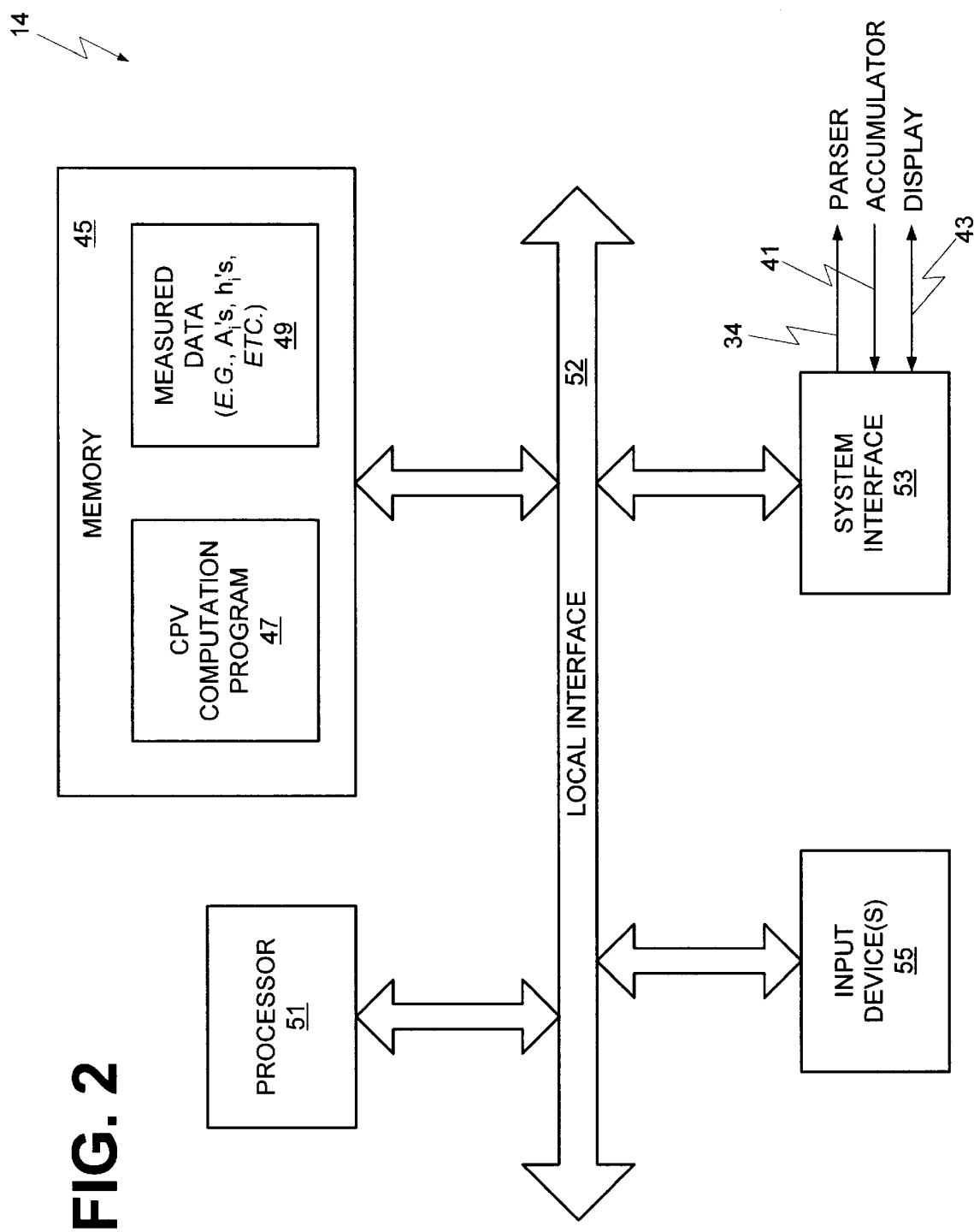
FIG. 2 is a low level block diagram of an example of a possible computer-based implementation of the CPV determination system of FIG. 1.

A detailed block diagram of the CPV determination system 14 is shown in FIG. 2. In architecture, in the preferred embodiment, the CPV determination system 14 is implemented as a computer-based or processor-based system, as illustrated in FIG. 2. The CPV determination system 14 includes a memory 45 (e.g., RAM, ROM, hard disk, etc., and combinations thereof) having a CPV computation program 47 for computing the CPV and the measured data 49, e.g., $A_i$'s and/or $h_i$'s and timing stamps, received from the ultrasound imaging system 12.

A processor 51 is in electrical communication with the memory 45 via a local interface 52, for example, one or more buses or interconnections. A processor 51 executes the CPV computation program 47 and operates upon the measured data 49 in order to produce CPVs.

In an alternative configuration, the CPU 13 (FIG. 1) can be assigned to execute the CPV computation program 47, instead of the processor 51 or in combination therewith.

A system interface 53 interconnects the CPV determination system 14 with the B-mode ultrasound imaging system 12, particularly, the parser 32 via connection 34, the accumulator 38 via connection 41, and the display 26 via connection 43. In essence, the system interface 53 includes a suitable set of drivers and/or buffers, which are well known in the art.

One or more input devices 55, for example but not limited to, a keyboard, a mouse, a trackball, etc., are connected to the local interface 52 and are in electrical communication with the aforementioned elements of the CPV determination system 14. In the preferred embodiment, the user uses one or more input devices 55 to advise the parser 32 of a region of interest.

Figure 3:
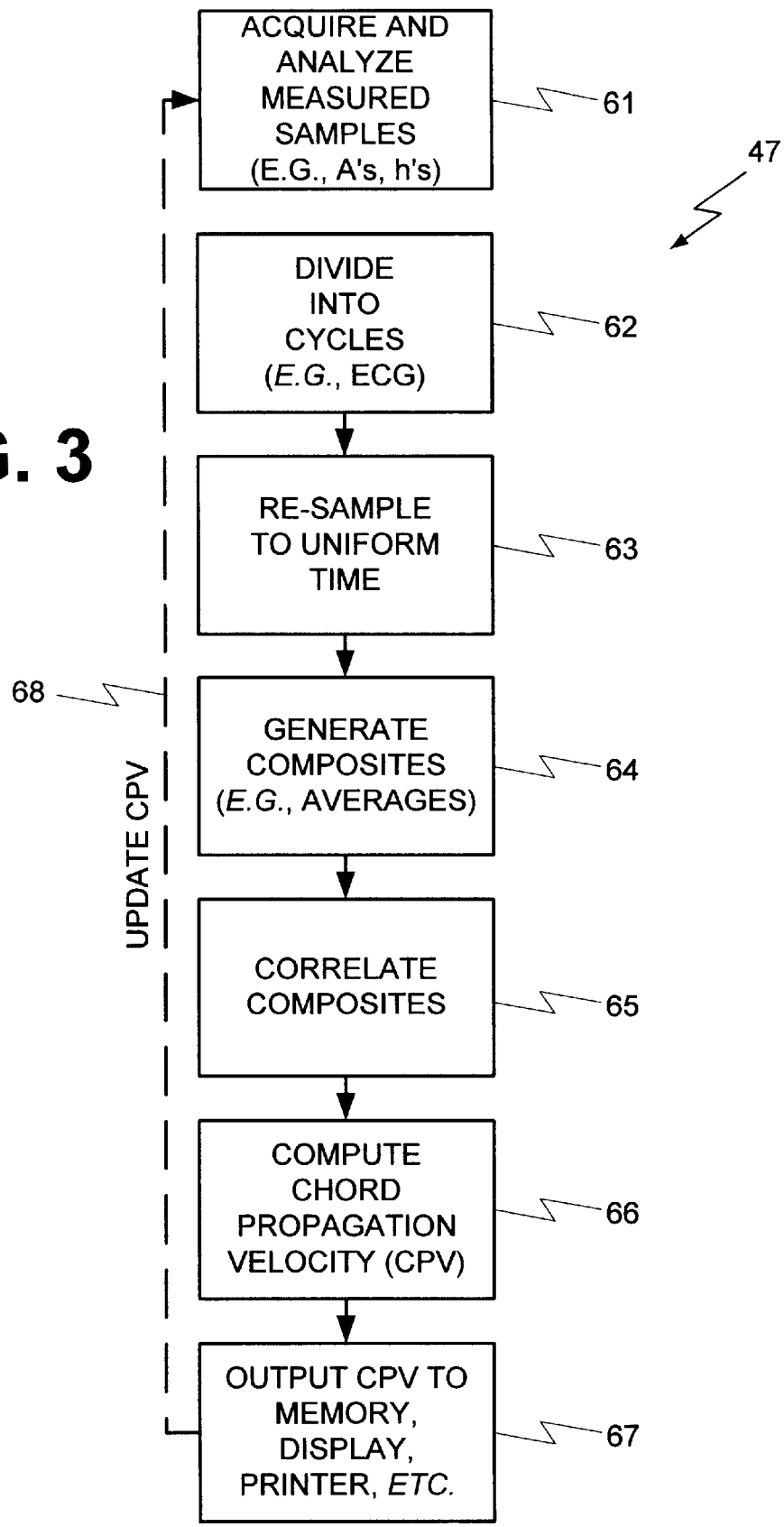
FIG. 3 is a flow chart showing the architecture, functionality and operation of an example of a possible implementation of the CPV determination system of FIG. 2 in the form of software or firmware.

The architecture, functionality, and operation of the CPV computation program 47 (FIG. 2) is illustrated by way of a flow chart in FIG. 3. With reference to FIG. 3, the CPV computation program 47 acquires the measured data 49, the areas $A_i$, or chords $h_i$, but preferably the areas $A_i$, from the memory 45 (FIG. 2). The remainder of this implementation will make reference to areas, but it should be understood that chords could be utilized instead. It is also possible that separate analyses could be performed on each separately as a check.

Next, as indicated by block 62 in FIG. 3, the samples are divided into cycles 75, as illustrated in FIG. 5. Preferably, the ECG signal is utilized as the synchronization timing signal to define the cycles 75. In essence, each heart beat defines the end of one cycle and the beginning of another cycle. Moreover, as mentioned, each area $A_i$ has been time stamped based upon its sampling time. The time stamps are compared with the cycles 75 to allocate the various points along each acoustic scan line with a particular cycle 75.

Referring again to FIG. 3, the CPV determination system 47 resamples the areas $A_i$, as denoted by block 63. The original sample rate of the areas $A_i$ and the heart beat associated with the ECG signal are generally asynchronous. The resampling process denoted by block 63 enables the compositing processing of the present invention, as will be described in detail hereinafter. In a sense, the resampling process enables analysis of the same physical area of the vessel 71 (FIG. 4) in different cycles.

Next, as shown in block 64 of FIG. 3, the CPV determination system 47 generates composites from the sets of areas $A_i$. The compositing process significantly improves the estimate of time shifts and minimizes noise associated with the ultrasound waveforms. More specifically, the areas $A_1$ from different cycles are averaged, for example, the areas from $A_1$ from different cycles are averaged, the areas $A_2$ from different cycles are averaged, and so on, in order to produce a composite $A_1$, a composite $A_2$, and so on, respectively. The compositing process works effectively because each measured area includes a signal level and noise that changes with each cycle so that the averaging process minimizes the noise level while maximizes the signal level. FIG. 5 shows composites $A_1, A_2, \ldots, A_k$. In general, the shift of the falling (or rising) edge of one composite to the next corresponds with the chord fluctuation of the vessel as a pressure pulse passes through the vessel.

With reference again to FIG. 3, after the compositing process indicated in block 64, the CPV computation program 47 performs a correlation process upon the composites, as denoted by block 65, in order to determine the time shift between composites $A_1, A_2, \ldots A_i$, in any desired combination. More specifically, with reference to FIG. 5, the time shift $t_s$ between composites is calculated. Entire waveforms or parts thereof may be analyzed in order to determine the time shifts between composites. Many techniques are known in the art for determining time shifts between signals. In the preferred embodiment, the falling edge associated with each composite that occurs after a heart beat 75 is focused upon by the CPV computation program 47. As an example, the points along composite $A_1$ and composite $A_2$ are mathematically correlated (multiplied together). The peak product of the correlation process is where the two composites are aligned. The peak yields the time shift $t_s$. Furthermore, the CPV between areas $A_1$ and $A_2$ is equal to the distance $(w_1+w_2)/2$ (effectively, the distance traveled by the pressure pulse) divided by the time shift $t_s$.

In order to obtain the precise peak of the correlation operation, it may be necessary or desirable to interpolate between two adjacent composites.

An alternative process for determining the time shift $t_s$ is to focus on the rising edges of the composites, instead of the falling edges.

Still another alternative process for determining the time shift $t_s$ would be to determine the mid-points of the valley or peak regions of each composite and then determine the difference between the mid-points on different composites.

In any technique that is selected to determine the time shift, there is a trade off between computational complexity and robustness. In other words, achieving greater precision in the calculation of the time shift necessarily adds computational complexity, which may or may not be desirable, depending upon system constraints.

With reference again to FIG. 3, as denoted in block 67, the CPV computation program 47 (FIG. 2) outputs the CPV value to a memory, a display, a printer, etc. In the preferred embodiment, the CPV determination system 47 outputs the CPV value at least to the display 26 (FIG. 1), as indicated by reference arrow 43 (FIG. 1). Furthermore, the system 47 can be configured, optionally, to update the CPV periodically at equal or unequal time intervals, as indicated by dashed arrow 68 in FIG. 3. An update merely involves repeating the foregoing steps that are shown in FIG. 3.

Figure 6A:
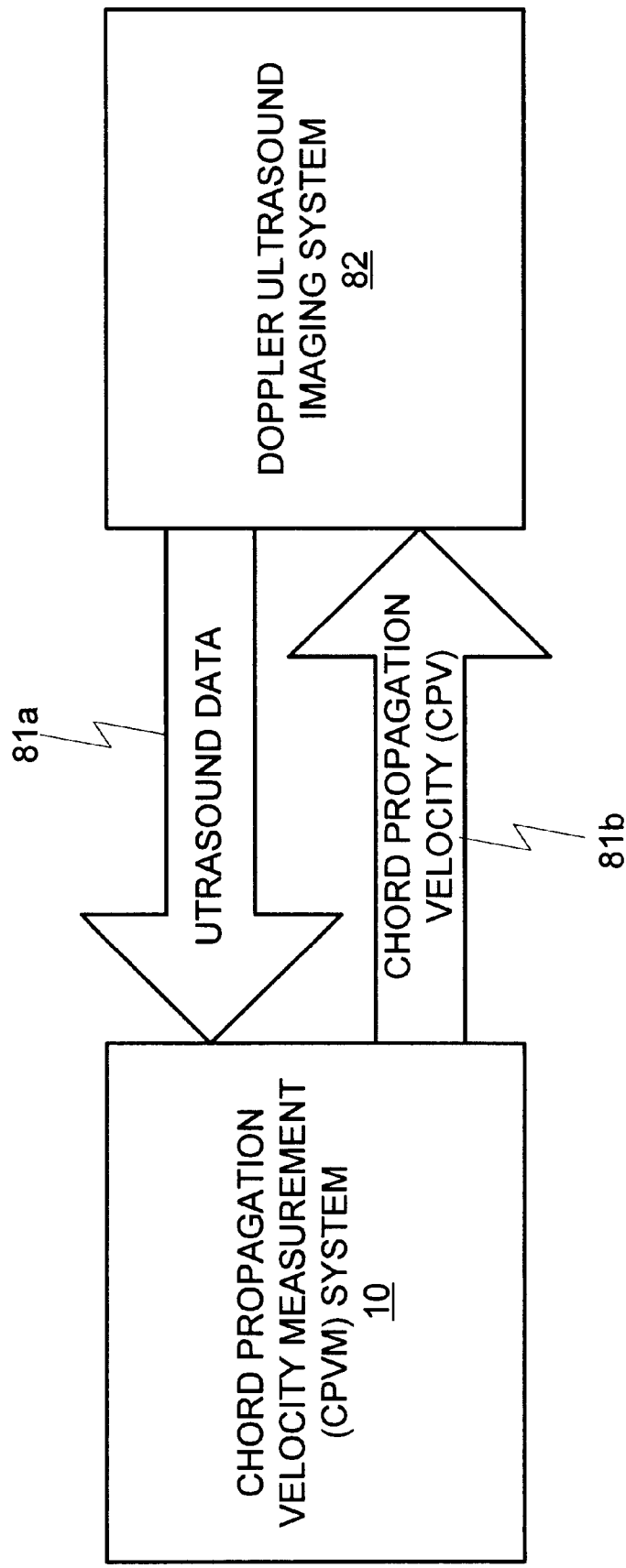
FIG. 6A is a high level block diagram of the chord propagation velocity (CPV) measurement (CPVM) system of the present invention, which is associated and in electrical communication with a doppler ultrasound imaging system.

By way of a high level block diagram, FIG. 6A shows the CPVM system 10 of the present invention used in connection with, for example but not limited to, a doppler ultrasound imaging system 82. Generally, the CPVM system 10 monitors ultrasound data 81a provided to it by the doppler ultrasound imaging system 82 and enhances the functionality of the doppler ultrasound imaging system 82 by providing a CPV 81b associated with a body part, such as a blood vessel in a living thing. As mentioned, the CPV 81b is indicative of the stiffness of the body part. Preferably, the CPV 81b is displayed, printed, or otherwise output by the CPVM system 10 to the user of the doppler ultrasound imaging system 82, in real time if desired, to permit analysis and evaluation of the body part by the user.

In architecture, the doppler ultrasound imaging system 82 can be any suitable, conventional or custom system and can be implemented in hardware, software, firmware, or a combination thereof. Many different types are known in the art and are commercially available. As nonlimiting examples, the doppler ultrasound imaging system 82 could be any of the following commercially available systems: the SONOS 2000, the SONOS 2500, or the SONOS 5500, all of which are manufactured by the Hewlett-Packard Company, U.S.A., or the Model XP10, which is manufactured by Acuson Corp., U.S.A.

Figure 6B:
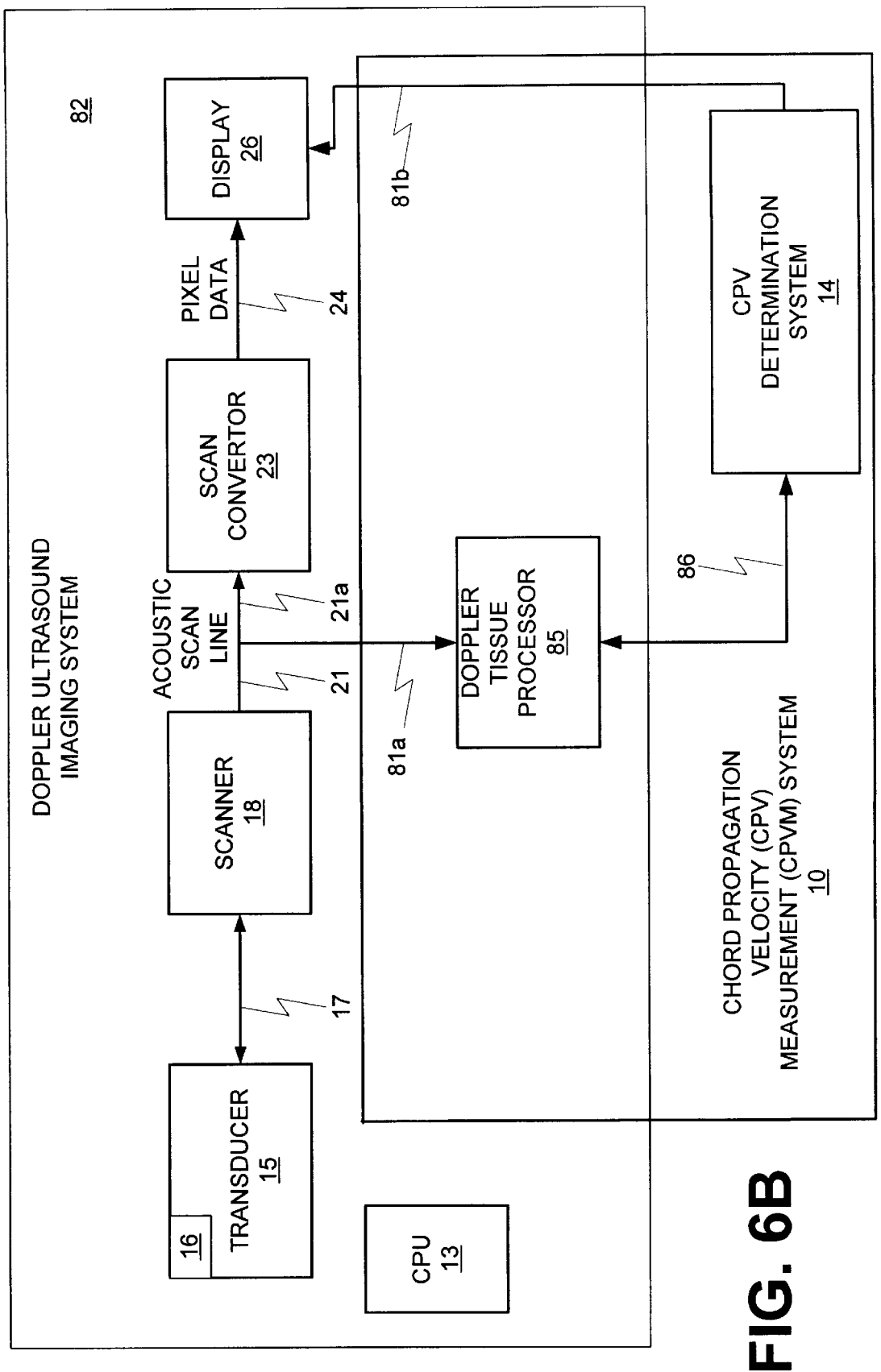
FIG. 6B is a low level block diagram of examples of possible implementations of the CPVM system and of the doppler ultrasound imaging system of FIG. 1, as interconnected.

The CPVM system 10 of the present invention can be implemented in hardware, software, firmware, or a combination thereof. FIG. 6B is a low level block diagram of an example of a possible implementation of the CPVM system 10 as used in connection with the doppler ultrasound imaging system 82 of FIG. 6A. As shown in FIG. 6B, the CPVM system 10 includes a doppler tissue processor 85 interconnected with the CPV determination system 14. In general, the doppler tissue processor 85 implements doppler tissue imaging.

Although not limited to this particular implementation, an example of a possible implementation of the doppler tissue processor 85 is described in U.S. Pat. No. 5,285,788, which is assigned to Acuson Corp., U.S.A., which is essentially that which is implemented in Acuson's Model XP10, and which is hereby incorporated herein by reference as if set forth in full hereinbelow. Presently, the preferred embodiment of the doppler ultrasound imaging system 82 is the SONOS 2000, the SONOS 2500, the SONOS 5500, or the Model XP10. Furthermore, in the foregoing types of doppler ultrasound imaging systems 82, the doppler tissue processor 85 is a standard commercially available option.

With any of these implementations, the doppler tissue processor 85 receives acoustic scan lines 21, 81a from the scanner 18 and analyzes the lines for motion of tissue. In essence, it analyzes the movement of the speckle pattern (pseudo-random) to produce changes in the cross sectional areas $A_i$, or $\Delta A_i$, and/or changes in the chords $h_i$, or $\Delta h_i$. The CPV determination system 14 is configured to analyze the $\Delta A_i$'s and/or $\Delta h_i$'s, instead of $A_i$'s and/or $h_i$'s as in the embodiment involving the B-mode system 12, and produce CPVs from them, just as CPVs were produced from $A_i$'s and/or $h_i$'s. In this embodiment, the composites of the $\Delta A_i$'s and/or $\Delta h_i$'s as well as $\Delta A_i$'s and/or $\Delta h_i$'s themselves are in fact velocity versus time waveforms.

It should be emphasized that the above-described embodiments of the present invention, particularly, any "preferred" embodiment(s), are merely possible examples of implementations that are merely set forth for a clear understanding of the principles of the invention. Furthermore, many variations and modifications may be made to the above-described embodiments of the invention without departing substantially from the spirit and principles of the invention. All such modifications and variations are intended to be taught by the present disclosure, included within the scope of the present invention, and protected by the following claims.

Therefore, at least the following is claimed:

1. A method for quantifying stiffness of a region of a body, comprising the steps of:
    acquiring a plurality of measured samples from different subregions along a longitudinal span of the body region for each of a plurality of different electrocardiogram (ECG) cycles;
    deriving a plurality of composites, one for each subregion, by combining corresponding samples from different ECG cycles; and
    producing a chord propagation velocity based upon said plurality of composites, said chord propagation velocity being indicative of the stiffness.

2. The method of claim 1, further comprising the steps of:
    determining a plurality of cross sectional areas from different subregions along said longitudinal span, each said cross sectional area based upon a chord length and width; and
    deriving said composites by mathematically combining corresponding areas from different ECG cycles.

3. The method of claim 1, further comprising the steps of:
    determining chord lengths from different subregions along said longitudinal span based upon said samples; and
    deriving said composites by mathematically combining corresponding chord lengths from different ECG cycles.

4. The method of claim 1, further comprising the step of mathematically averaging said corresponding samples in order to derive said composites.

5. The method of claim 1, further comprising the steps of:
    displaying said chord propagation velocity on a computer display; and
    updating said chord propagation velocity on the computer display over time.

6. The method of claim 1, further comprising the steps of:
    producing a plurality of said chord propagation velocities, each corresponding with a different subregion of the region; and
    displaying a graph on a computer display showing said chord propagation velocities versus said subregions.

7. The method of claim 1, further comprising the steps of:
    determining said chord propagation velocity by estimating the time shift between said composites, said chord propagation velocity being determined by utilizing estimated time shifts and distances between subregions.

8. The method of claim 1, further comprising the step of:
    determining a time shift of a feature associated with said composites in order to produce said chord propagation velocity.

9. The method of claim 8, wherein said feature is a falling edge of a change in chord length caused by pumping activity produced by a heart in the body.

10. The method of claim 1, wherein said body is a living thing and said region is a blood vessel within the body.

11. The method of claim 1, further comprising the step of utilizing a brightness mode ultrasound imaging system to acquire said samples.

12. The method of claim 1, further comprising the step of utilizing a doppler ultrasound imaging system to acquire said samples.

13. The method of claim 1, wherein said samples and said ECG cycles are asynchronous and further comprising the step of:
    re-sampling said measured samples to normalize them relative to said ECG cycles, prior to deriving said plurality of said composites.

14. The method of claim 1, further comprising the step of acquiring said chord samples by using a linear probe.

15. The method of claim 1, further comprising the step of acquiring said chord samples by using a sector probe.

16. The method of claim 1, further comprising the step of acquiring said chord samples by using a curved linear array probe.

17. A system for quantifying stiffness with a region of a body, comprising:
    first means for acquiring a plurality of measured samples from different subregions along a longitudinal span of the body region for each of a plurality of different electrocardiogram (ECG) cycles;

second means for deriving a plurality of composites, one for each subregion, by combining corresponding samples from different ECG cycles; and third means for producing a chord propagation velocity based upon said plurality of composites, said chord propagation velocity being indicative of the stiffness.

18. An ultrasound imaging system, comprising:

an ultrasound transducer designed to transmit and receive ultrasound signals;

an ultrasound scanner in electrical communication with said transducer, said scanner designed to produce acoustic scan lines based upon said ultrasound signals;

a user output mechanism in electrical communication with said scanner, said user output mechanism designed to produce an image generated by said acoustic scan lines;

a user input mechanism in electrical communication with said scanner, said user input mechanism designed to permit a user to identify a region of interest in said image;

a processor in electrical communication with said scanner, said processor designed to acquire a plurality of measured samples from different subregions along a longitudinal span of a body region within said region of interest for each of a plurality of different electrocardiogram (ECG) cycles, to derive a plurality of composites, one for each subregion, by combining corresponding samples from different ECG cycles, and to produce a chord propagation velocity based upon said plurality of composites, said chord propagation velocity being indicative of the stiffness.

* * * * *